United States Patent
Parnas et al.

(10) Patent No.: US 7,695,970 B2
(45) Date of Patent: Apr. 13, 2010

(54) OPTICAL FIBER BASED FLUORESCENCE SENSOR FOR IN-SITU MEASUREMENT AND CONTROL OF FUEL CELLS

(75) Inventors: Richard S. Parnas, West Hartford, CT (US); Yatin P. Patil, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 1085 days.

(21) Appl. No.: 11/361,927

(22) Filed: Feb. 24, 2006

(65) Prior Publication Data

US 2006/0199270 A1 Sep. 7, 2006

Related U.S. Application Data

(60) Provisional application No. 60/658,781, filed on Mar. 4, 2005.

(51) Int. Cl.
*G01N 33/18* (2006.01)
*G01N 21/64* (2006.01)

(52) U.S. Cl. .............. 436/39; 422/82.05; 422/82.06; 422/82.07; 422/82.08; 422/82.11; 436/40; 436/166; 436/169; 436/172

(58) Field of Classification Search ... 422/82.05–82.11; 436/39–40, 166, 169, 172
See application file for complete search history.

(56) References Cited

U.S. PATENT DOCUMENTS

| | | | | |
|---|---|---|---|---|
| 3,697,226 A | * | 10/1972 | Hirschfeld et al. | 422/88 |
| 4,083,765 A | * | 4/1978 | Lawson | 205/788 |
| 4,433,238 A | * | 2/1984 | Adolfsson et al. | 250/227.23 |
| 4,681,855 A | * | 7/1987 | Huang | 436/39 |
| 4,693,953 A | * | 9/1987 | Torikai | 430/165 |
| 4,749,856 A | * | 6/1988 | Walker et al. | 250/227.11 |
| 5,036,704 A | * | 8/1991 | Pusatcioglu et al. | 73/335.02 |
| 5,212,099 A | * | 5/1993 | Marcus | 436/172 |
| 5,268,145 A | * | 12/1993 | Namba et al. | 422/57 |
| 6,521,185 B1 | * | 2/2003 | Groger et al. | 422/82.08 |
| 2002/0173040 A1 | * | 11/2002 | Potyrailo et al. | 436/2 |

OTHER PUBLICATIONS

Litwiler, K. S. et al, Analytical Chemistry 1991, 63, 797-802.*
Zinger B. et al, Sensors and Actuators B 1999, 56, 206-214.*
Eisenberg, A.; Yeager, H.L.; Editors American Chemical Society Symposium Series, No. 180: Perfluorinated Ionomer Membranes [Developed in Advance of the Topical Workshop on Perfluorinated Ionomer Membranes, Lake Buena Vista, Florida, Feb. 23-26, 1982], 1982.

(Continued)

*Primary Examiner*—Arlen Soderquist
(74) *Attorney, Agent, or Firm*—McCarter & English, LLP

(57) ABSTRACT

The present invention provides, a system and method for unobtrusively determining water content within a fuel cell. One embodiment of a system in accordance with the present invention includes a fuel cell body including an ionomeric membrane, water and a fluorophore contained therein. The system further includes a medium for permitting light transfer therein, such as an optical fiber, having opposing ends, wherein one end contacts or is disposed in a portion of the ionomeric membrane and the other end extends from the fuel cell body. The other end is preferably divided into at least two portions, one portion being operatively associated with a light source, and another portion being operatively associated with a spectrometer.

20 Claims, 9 Drawing Sheets

Fluorescence spectra of Nafion® membrane containing rhodamine-6G in a TGA pan at 80°C with loss of water

OTHER PUBLICATIONS

Zawodzinski, T.A., Jr.; Derouin, C.; Radzinski, S.; Sherman, R. J.; Smith, V.T.; Springer, T.E.; Gottesfield, S. Journal of the Electrochemical Society 1993, 140, 1041-1047.

Anantaraman, A.V.; Gardner, C.L. Journal of Electroanalytical Chemistry 1996, 414, 115-120.

Edmondson, C.A.; Stallworth, P.E.; Chapman, M.E.; Fontanella, J.J.; Wintersgill, M.C.; Chung, S.H.; Greenbaum, S.G. Solid State Ionics 2000, 135, 419-423.

Gebel, G. Polymer 2000, 41, 5829-5838.

Zawodzinski, T.A.; Davey, J.; Valerio, J.; Gottesfield, S. Electrochimica Acta 1995, 40, 297-302.

Bunce, N.J.; Sondheimer, S.J.; Fyfe, C.A. Macromolecules 1986, 19, 333-339.

Gonzalez-Benito, J.; Bravo, J.; Mikes, F.; Baselga, J. Polymer 2002, 44, 653-659.

Martin, O.; Pastoriza, A.; Mikes, F.; Baselga, J. Polymer International 2002, 51, 1207-1210.

Hakala, K.; Vatanparast, R.; Vuorimaa, E.; Lemmetyinen, H. Journal of Applied Polymer Science 2001, 82, 1593-1599.

Miller, K.E.; Krueger, R.H.; Torkelson, J.M. Journal of Polymer Science, Part B: Polymer Physics 1995, 33, 2343-2349.

Geuskens, G.; Soukrati, A. European Polymer Journal 2000, 36, 1537-1546.

Otsuki, S.; Adachi, K. Polymer Journal (Tokyo, Japan) 1994, 26, 343-348.

Bright, F.V.; Poirier, G.E.; Hieftje, G.M. Talanta 1988, 35, 113-118.

Glenn, S.J.; Cullum, B.M.; Nair, R.B.; Nivens, D.A.; Murphy, C.J.; Angel, S.M. Analytica Chimica Acta 2001, 448, 1-8.

Mohan, H.; Iyer, R.M. Journal of the Chemical Society, Faraday Transactions 1992, 88, 41-45.

Mohan, H.; Iyer, R.M. Analyst (Cambridge, United Kingdom) 1993, 118, 929-932.

Zhu, C.; Bright, F.V.; Wyatt, W.A.; Hieftje, G.M. Proceedings—Electrochemical Society 1987, 87-9, 476-483.

Hinatsu, J.T.; Mizuhata, M.; Takenaka, H. Journal of the Electrochemical Society 1994, 141, 1493.

Rieke, P.C.; Vanderborgh, N.E. Journal of Membrane Science 1987, 32, 313-328.

Buchi, F.N.; Scherer, G.G. Journal of the Electrochemical Society 2001, 148, A183-A188.

Andreaus, B.; Scherer, G.G. Solid State Ionics 2004, 168, 311-320.

Sridhar, P.; Perumal, R.; Rajalakshmi, N.; Raja, M.; Dhathathreyan, K.S. Journal of Power Sources 2001, 101, 72-78.

Eikerling, M.; Kharkats, Y.I.; Kornsheve, A.A.; Volfkovich, Y. M. Journal of the Electrochemical Society 1998, 145, 2684-2699.

\* cited by examiner

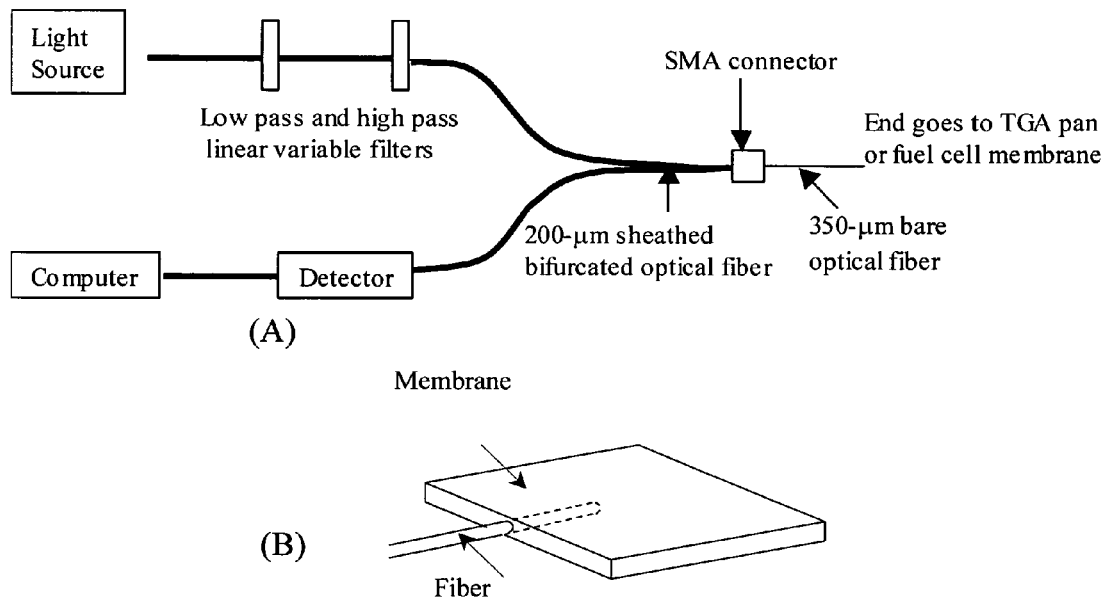
FIG. 1. (A) Schematic of the fluorescence instrument setup; (B) Fiber location in the membrane

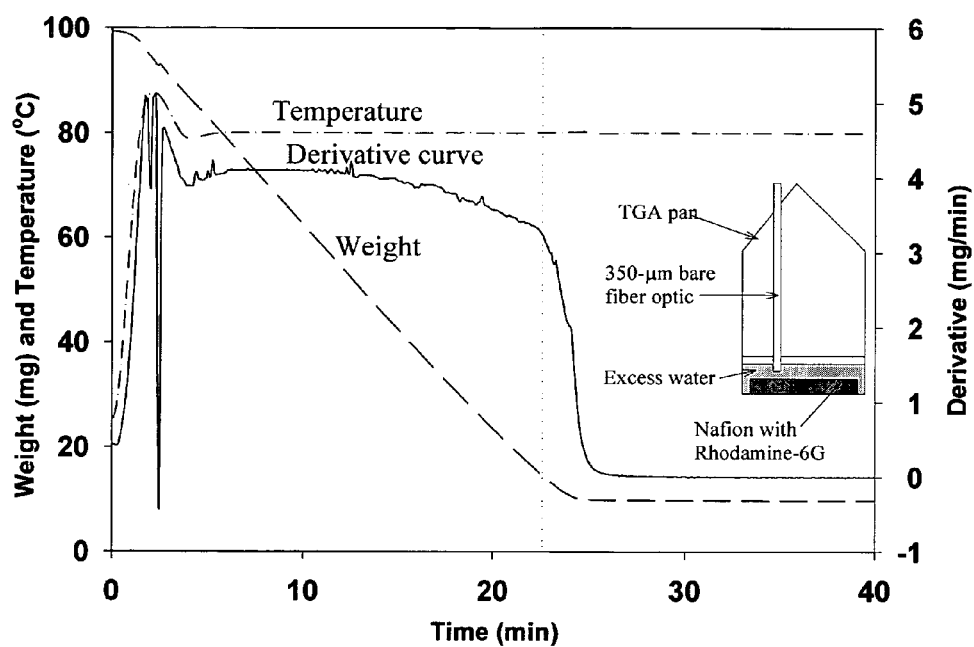
FIG. 2. TGA weight loss curve of Nafion® containing Rhodamine-6G with excess water

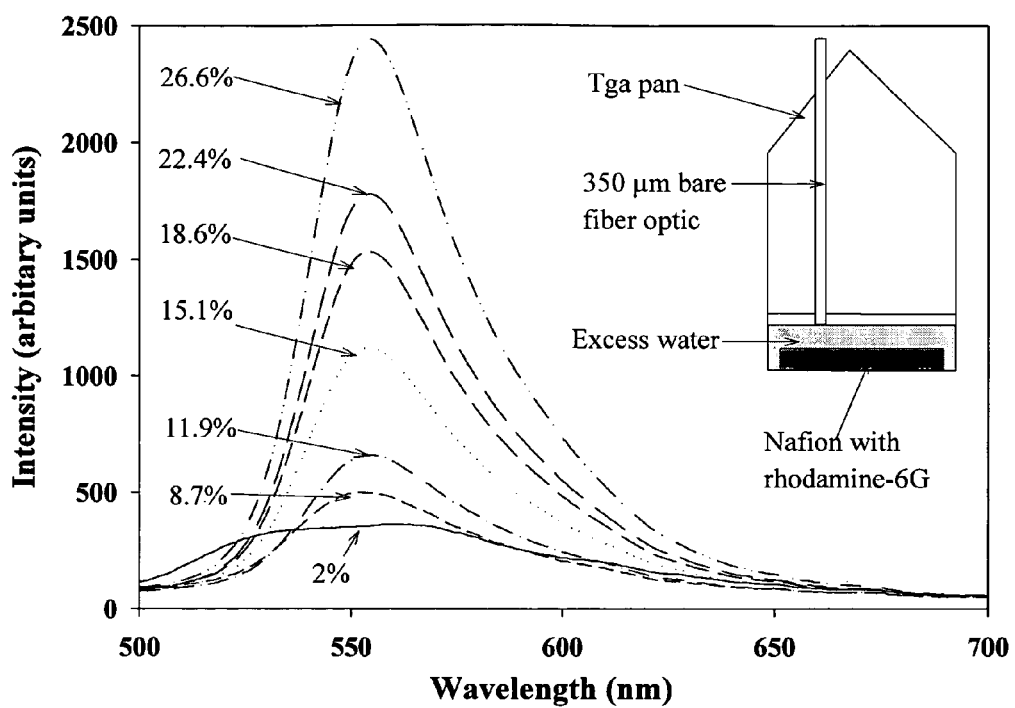
FIG. 3. Fluorescence spectra of Nafion® membrane containing rhodamine-6G in a TGA pan at 80°C with loss of water

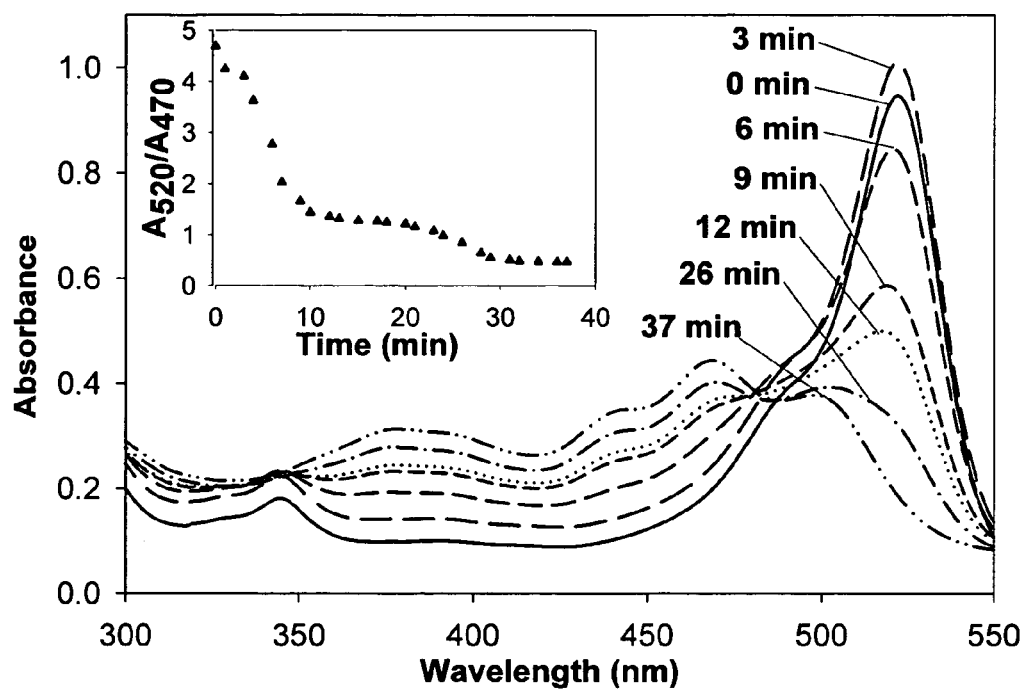
FIG. 4. Absorption spectra of Nafion® containing Rhodamine-6G while drying

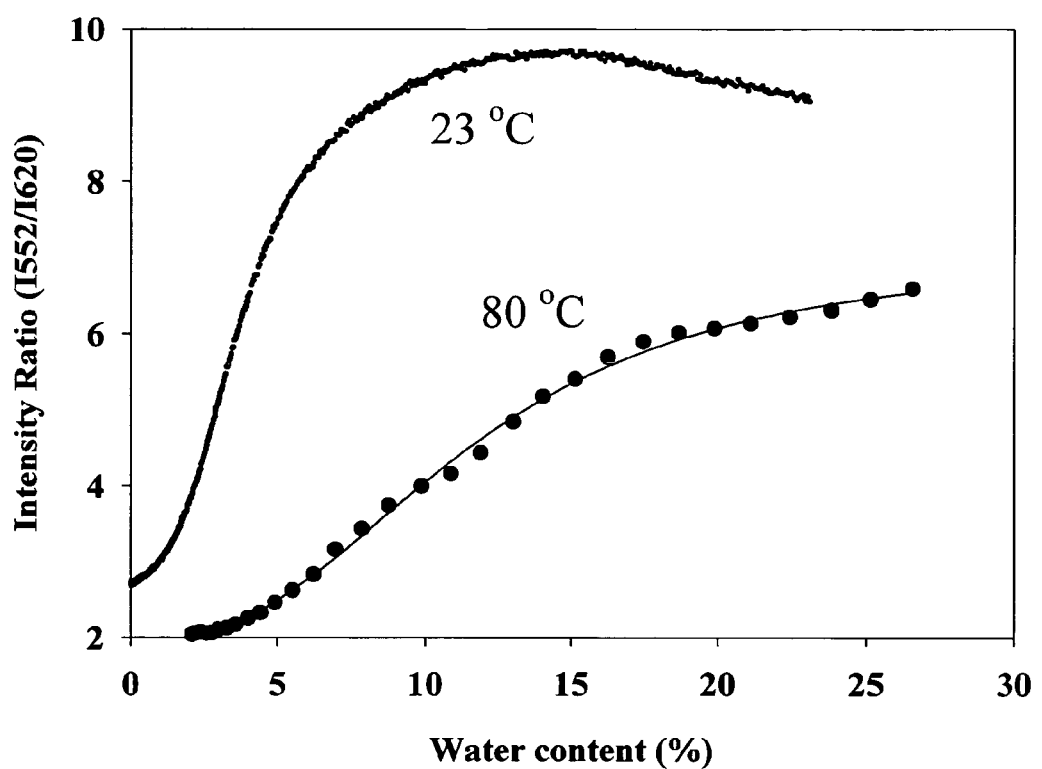
FIG. 5. Fluorescence intensity ratio as a function of Nafion® water content at 23 and 80°C

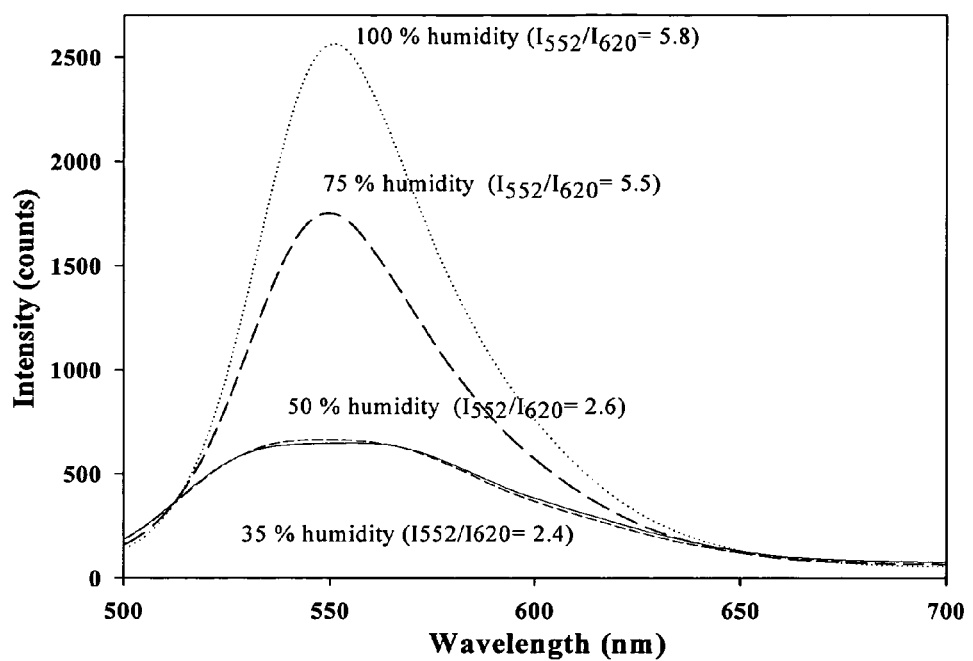
FIG. 6. Fluorescence spectra at different humidity levels of the feed gases

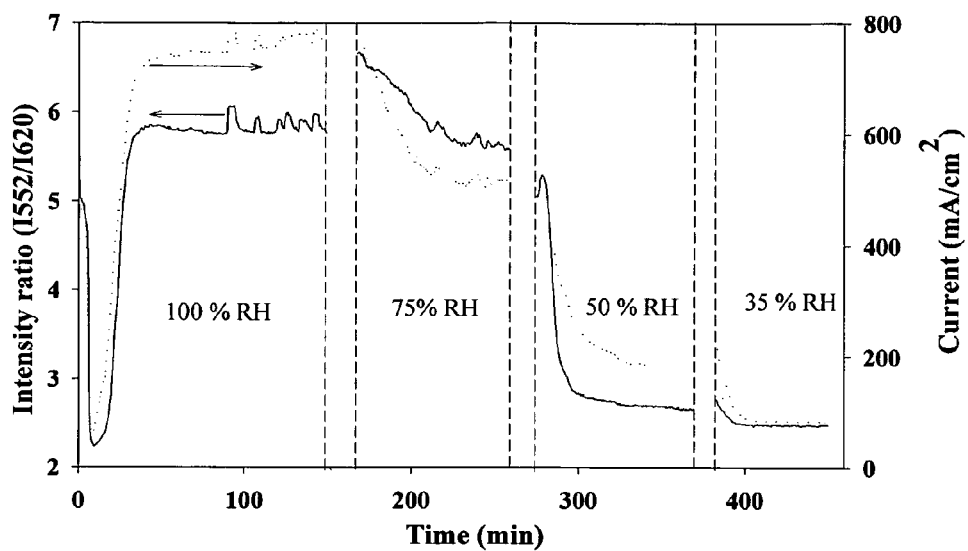
FIG. 7. Fluorescence ratio and current as a function of time

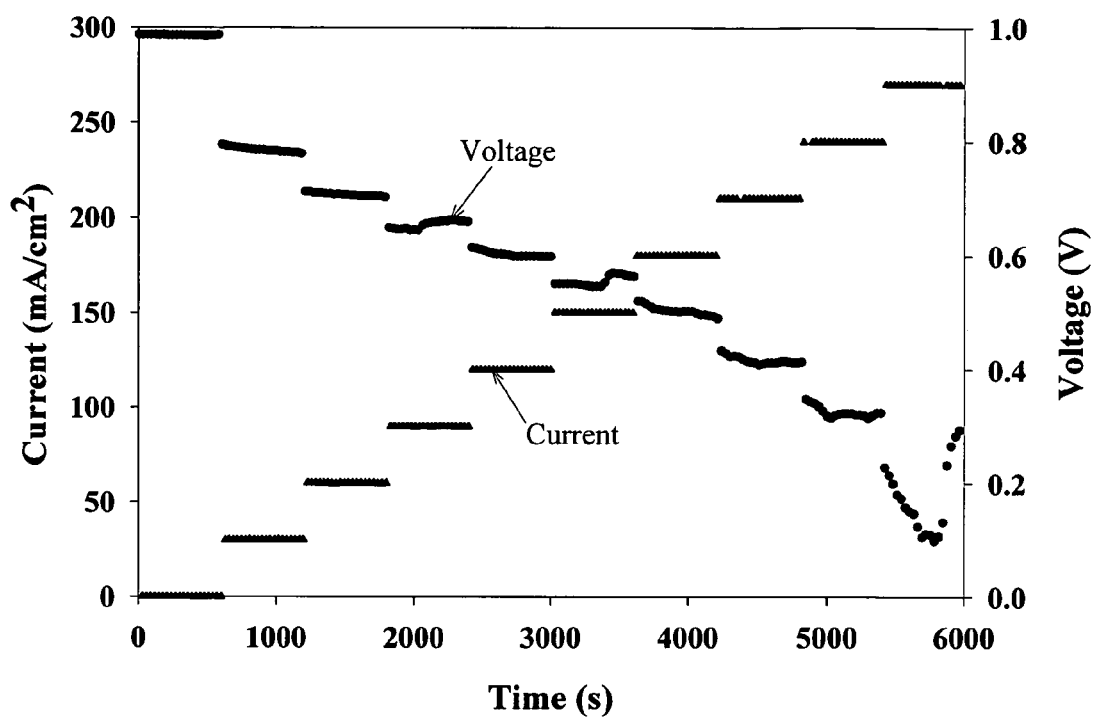
FIG. 8A. Current and voltage trend as a function of time for fuel cell operated at 75% RH and 80°C

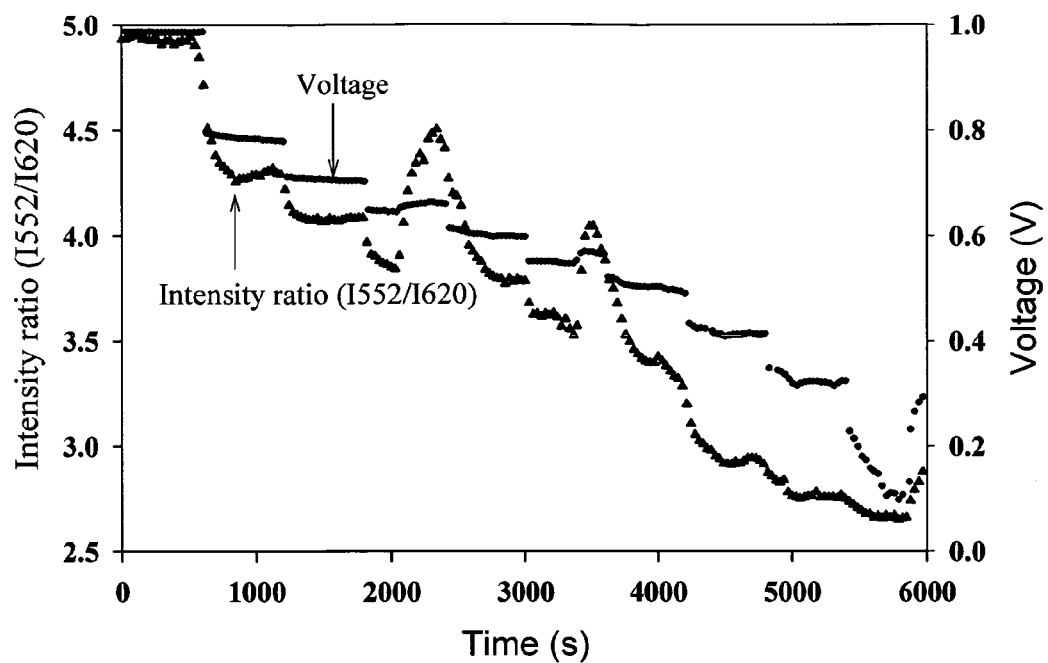
FIG. 8B. Fluorescence intensity ratio and voltage trend as a function of time for fuel cell operated at 75% RH and 80°C

OPTICAL FIBER BASED FLUORESCENCE SENSOR FOR IN-SITU MEASUREMENT AND CONTROL OF FUEL CELLS

CROSS-REFERENCE TO RELATED APPLICATION

This application claims the benefit of priority from U.S. Provisional Patent Application Ser. No. 60/658,781 filed Mar. 4, 2005.

BACKGROUND OF THE INVENTION

1. Field of the Invention

The present invention relates to the operation of a proton exchange membrane fuel cell, and in particular, a system and method for using fiber optic fluorescence spectroscopy to detect changes in the Nafion® membrane water content in a fuel cell at several operating conditions.

2. Brief Description of the Related Art

Polymer Electrolyte Fuel Cells ("PEFCs," which are also referred to as Proton Exchange Membrane Fuel Cells, or "PEMFCs") are well suited for a variety of applications by virtue of their efficiency, environment friendly nature and high power densities.

A PEFC generally consists of a membrane sandwiched between two electrodes that are typically made from platinum or platinum-ruthenium supported on carbon, along with ionomeric material or electrolytes to promote protonic conductivity, such as sulfonic acid groups disposed in the membrane. Porous carbon backings (with a micro porous carbon layer on one side) are used to distribute the fuel and oxidant gases uniformly throughout the active electrode area, to conduct electrons and facilitate water transport, among other things. The gases enter the system through flow fields machined into graphite plates, which also serve as current collectors.

Fuel, typically hydrogen ($H_2$) or methanol, is electrochemically oxidized at one of the electrodes, which is called the anode, to form protons and electrons. The protons diffuse through the polymer electrolyte membrane ("PEM") to the other electrode, called the cathode, where they combine electrochemically with the oxidant, which is usually air, to produce water. The electrons needed to complete this reduction reaction are directed to the cathode via an external circuit electrically connecting the anode and cathode.

One of the most common PEMs in use today for solid electrolyte for $H_2/O_2$ polymer electrolyte fuel cells is Nafion®, a commercially available perfluorinated sulfonic acid ionomer manufactured by E.I. du Pont de Nemours & Co. Nafion® is a copolymer of tetrafluoroethyelene and sulfonyl fluoride vinyl ether and has reverse micelle morphology in the dry state, where the ionic clusters are dispersed in a continuous tetrafluoroethyelene phase. The Teflon-like inert hydrophobic backbone provides chemical, mechanical and thermal stability, whereas the pendant sulfonic acid group of the vinyl ether imparts hydrophilicity and, most importantly, proton conductivity.

While this membrane performs very well in a saturated environment, its charge carriers are hydrated protons, resulting in membrane proton conductivity that is largely influenced by water content. Proton conductivity decreases considerably when the water content in the operating environment is low (i.e., low relative humidity conditions). When the water content in the membrane is at or above a critical level, the ionic domains swell with water absorption to form interconnected proton-conducting channels. The conductivity increases because this swelling reduces the separation between the micelles and aids in the transport of proton. However, if the water content is too great the ionic groups become diluted which decreases the concentration of the protons therein and reduces proton conductivity.

The proton transport in the membrane is known to occur via hydronium ions (electro-osmotic drag), which results in drying of the anode. To prevent anode drying, the hydrogen gas is typically saturated with water vapor. The water generated at the cathode and that carried by electro-osmotic drag create a water gradient resulting in back diffusion of the water towards the anode. The water distribution throughout the membrane is determined by the membrane water uptake, the spatial variations in fuel (i.e., $H_2$) supply and the interplay between electro-osmotic drag and back diffusion. Uneven distribution of the feed in the gas distribution channels and catalyst poisoning can lead to non-uniform electrochemical reaction and uneven water content in the x-y plane of the membrane. In sum, water management is crucial, and determining the in-situ water content can be used to greatly improve the efficiency of fuel cell operation.

Gravimetric analysis, Near-IR and NMR spectroscopy can quantify the water content, but in-situ measurements are difficult. An estimate of the water content inside the cell can be obtained using water mass balancing, that is, by measuring the relative humidity of the incoming and outgoing streams at steady state, but this does not truly represent the membrane water content as water can condense in the gas distribution channel and gas diffusion layer. The membranes within the fuel cell are thin and coated with electrodes on either side, and the cell is clamped under high pressure for a good electrical circuit and made leak proof, making incorporation of a conventional sensor within the fuel cell therein extremely difficult.

Thus, what is needed is a system and method for accurately measuring water content in PEFCs without compromising the integrity or disturbing the normal fuel cell arrangement. As is readily apparent, such a system and method would provide higher efficiency PEFC operation and yield advantages in fuel cell applications which may not have been contemplated due to the limitations described above.

SUMMARY OF THE DISCLOSURE

The present invention improves upon and solves the problems associated with the prior art by providing, among other things, a system and method for unobtrusively (i.e., not harmful to normal operations) determining water content within a fuel cell.

In particular, a system in accordance with the present invention includes a fuel cell body including an ionomeric membrane, water and a fluorophore contained therein. The system further includes a medium for permitting light transfer therein, such as an optical fiber, having opposing ends, wherein one end contacts or is disposed in a portion of the ionomeric membrane and the other end extends from the fuel cell body. The other end is preferably divided into at least two portions, one portion being operatively associated with a light source, and another portion being operatively associated with a spectrometer.

In one embodiment of the aforementioned system, the fluorophore is one which is sensitive to membrane water content. Preferably the fluorophore is Rhodamine-6G or the like.

In another embodiment of the aforementioned system, the ionomeric membrane is fabricated of a polymer electrolyte. Preferably the ionomeric membrane is fabricated of Nafion® or the like.

The present invention is also directed to a method for determining water content within a fuel cell having water and a fluorophore therein, which includes using a medium permitting light transfer therein, such as an optical fiber, contacting or disposed in an ionomeric membrane at one end and operatively associated with a light source and a spectrometer at the other end. Preferably, the other end operatively associated with the light source and spectrometer is divided into at least two separate portions. The light source is activated and the spectrometer is used to obtain fluorescence spectroscopy which is used to detect changes in the membrane water content.

The method of the present invention can be used to predict the dynamic response of the fuel cell during startup, operating condition changes, and changes during many small perturbations.

The present invention is also directed to a sensing device for in-situ measurement of membrane water content in fuel cells which includes an optical fiber having a first end disposed in a fuel cell membrane and a second end from the membrane and having at least two portions, wherein one portion is operatively associated with a light source and another portion is operatively associated with a spectrometer.

These and other aspects of the present invention will become more readily apparent to those having ordinary skill in the art from the following description of the invention taken in conjunction with the drawings.

BRIEF DESCRIPTION OF THE FIGURES

So that those having ordinary skill in the art to which the present invention pertains will more readily understand how to make and use the present invention, an embodiment thereof will be described in detail with reference to the drawings, wherein:

FIG. 1A is a schematic of an exemplary fluorescence instrument setup constructed in accordance with the present invention;

FIG. 1B is schematic of an exemplary an optical fiber disposed in a fuel cell membrane in accordance with the present invention;

FIG. 2 is a plot of Thermogravimetric Analyzer (TGA) weight loss curve of Nafion® containing Rhodamine-6G with excess water;

FIG. 3 is a fluorescence spectra of Nafion® membrane containing Rhodamine-6G in a TGA pan at 80° C. with loss of water;

FIG. 4 is an absorption spectra of Nafion® containing Rhodamine-6G while drying;

FIG. 5 is a fluorescence intensity ratio as a function of Nafion® water content at 23 and 80° C.;

FIG. 6 is a fluorescence spectra at different humidity levels of the feed gases;

FIG. 7 is a fluorescence ratio and current as a function of time at 80° C. and 0.2V;

FIG. 8A is a current and voltage trend as a function of time; and

FIG. 8B is a fluorescence intensity ratio and voltage trend as a function of time for fuel cell operated at 75% RH and 80° C.

ENABLING DESCRIPTION OF THE INVENTION

It has been found that the water content can be measured without disturbing the PEFC if the water sensor is a part of the PEM. Importantly, the sensor should be sensitive to the wide variations in membrane water content under both operating and shut down conditions.

It has also been discovered that near IR measurements can quantify water content in polymer systems. However, near IR probes based on fiber optics are often too large to use in a fuel cell. A number of commercial spectrometer manufacturers sell fiber optic couplers for their spectrometers, and the same has been found to be useful for this application. However, such instrumental arrangements typically require that both ends of the fiber protrude from the sample. In the case of a fuel cell, that would require the fiber to pass completely through the membrane, and result in a length-averaged signal. Distal end fluorescence measurements as described herein provide good spatial resolution. Moreover, fluorescence can measure many other things besides water and detailed chemistry.

Incorporating a pH-sensitive fluorescence molecule in the membrane can provide information regarding the pH, and indirectly water content. The fluorescence of a fluorophore is extremely sensitive to its local environment (polarity) and viscosity or both. The excited fluorophore molecule is stabilized by an effective dielectric coupling with the dipoles of the surrounding chemical groups. This lowers the energy of the excited state, resulting in emission at longer wavelength.

Along with gravimetric analysis, the fluorescence technique has been applied to determine water content in nonionic polymers like epoxy, polyurethane and poly (vinyl acetate). The technique was also used to estimate water content in highly water absorbing systems like hydrogels and colloids. All those reported studies were done at room temperature as simultaneous fluorescence and gravimetric analysis at elevated temperature requires very good control over the humidity of the chamber containing the balance.

A reference to Otsuki and Adachi listed below disclosed a relative humidity sensor based on the fluorescence response of 5-dimethylaminonaphthalene-1-sulphonic acid in hydroxypropyl cellulose. Nafion® membranes containing certain fluorescence molecules have been proposed as sensors to detect trace amounts of ionic species in water and impurities in organic solvents. Such applications were also explored at room temperature.

For the present invention, molecules sensitive to changes in the membrane water content were sought. A reference to Mohan and Iyer reported a change in the optical absorption of Rhodamine-6G in Nafion® at different water contents. Based on its optical absorption and emission under neutral and acidic solutions, it was used to indirectly measure the high $H^+$ ion concentration in aqueous solution at room temperature. The Mohan and Iyer reference involved indirectly measuring high $H^+$ ion concentrations in aqueous solution using uv-vis absorption spectroscopy. This reference also disclosed a decrease in fluorescence intensity with increasing $H^+$ ion concentration of the solution in which the membrane was immersed, and also during drying of water soaked Nafion® membrane containing rhodamine-6G.

In a reference to Zhu et al, a fiber optic humidity sensor based on Nafion® membrane containing 1 wt % Rhodamine-6G was disclosed. In this reference, the fluorescence intensity at a particular wavelength was used to quantify the humidity of air at room temperature. However, the fluorescence intensity can vary with fluctuations in the light source and concentration of the fluorophore. The concentration of the fluorophore (1 wt %) was very high which may have caused inner filtering, where the emission is absorbed by the surrounding fluorophore.

The present invention includes several improvements over past work, among other things. The present invention includes an improved data analysis technique that relies on the ratio of fluorescence intensity at two wavelengths. The technique of the present invention has been found to be more robust for measuring Nafion® membrane water content than that disclosed in previous methods, which typically used the intensity at a single wavelength.

In addition, the membrane preparation technique of the present invention allows the collection of fluorescence spectra via fiber optics from the membrane while in the operating fuel cell operating at a variety of conditions. Inexpensive yet sensitive equipment allows for low dye concentrations, well below the inner filtering regime. Data collection at the realistic fuel cell operating temperature of 80° C. is demonstrated, although generating a good calibration curve has put limitations on quantitative interpretation of the data.

Experimental Information

Materials and Membrane Preparation

A commercially available 20 wt % Nafion® solution in water-isopropanol was obtained from Solution Technology Inc. (equivalent weight 1100 g/mol sulfonic groups). Rhodamine-6G was obtained from Sigma-Aldrich and was used without further purification. A very dilute Nafion®-dye solution was made by mixing the 20 wt % Nafion® solution with a $4.12 \times 10^{-4}$ mol/L ethanol solution of Rhodamine-6G. The membrane was cast by pouring the 20 wt % Nafion® solution on a 4-cm×4-cm glass plate with a 350-μm bare optical fiber (OZ Optics) in it. The fiber was positioned parallel to the membrane surface with its end lying at the center of the membrane. FIG. 1B provides the general location and placement of the optical fiber in this experiment. It should be readily apparent that the fiber could be located in many different portions of the membrane.

Before embedding the bare optical fiber, its tip was coated with the Nafion® dye solution. The final concentration of the dye in the dry membrane at the tip of the fiber was calculated to be $5.75 \cdot 10^{-7}$ mol/g. The addition of such a low concentration of dye would advantageously have no effect on the Nafion® water absorption and transport properties. The thickness of the cast membrane was 400 μm, which is higher than the regularly used Nafion® membrane (50-175 μm). Membranes of varying thickness can be used with the present invention, and it has been found that greater thickness generally increases the membrane resistance and reduces cell performance. The membrane used for this experiment incorporated readily available optical components. Thinner membranes could be used in accordance with the present invention with smaller optical fibers and corresponding focusing optics.

The membrane was coated with the catalyst obtained from Tanaka Kikinzoku Kogyo K. K., Japan by the decal transfer process. The catalysts, 46.5 wt. % Pt/C on the cathode and 30.1% Pt-23.4% Ru/C on the anode were impregnated with Nafion® solution. The catalyst loading used for this study was high and may be changed without compromising the functionality of the present invention. The electrodes were first screen printed on a Teflon sheet and then hot pressed with the membrane between two rubber sheets at 150° C. for 10 minutes under 207 kPa (30 psig) pressure. The membrane electrode assembly (MEA) was assembled in a fuel cell having an area of 5 $cm^2$ with series sweep flow fields (Electrochem Inc.; model no. FC05-01SP). The cell was closed by applying a uniform torque of 3.5 N m to each of the eight bolts. High purity hydrogen and oxygen, passed through water-filled sparger bottles, were used. The humidity of the gases was controlled by controlling the temperature of the sparger, and was checked by dew-point measurements. The cell temperature was maintained at 80° C. for all the experiments.

Instrumental Setup

Fluorescence spectra were recorded using an Ocean Optics fiber optic fluorescence spectrometer (HR 2000) equipped with an attachment to connect bare optical fiber. UV-Vis spectra were recorded with a Perkin-Elmer Lambda 6 UV-Vis spectrometer. A TA Instruments TGA 2950 Thermogravimetric Analyzer (TGA) was used to measure the water loss in Nafion® membranes.

As shown in FIG. 1A, bifurcated optical fiber (UV-Vis grade, made by Ocean Optics) was used to excite and collect the fluorescence signal from the membrane. The two ends of the bifurcated fiber, one connected to a high power Xenon light source (HPX-2000) and the other connected to the detector (Ocean Optics HR 2000) were combined into a SMA 905 terminated single optical fiber. The core diameter of the fiber was 200 μm, while the outside diameter including the protective claddings was 8 mm. The combined fiber excites as well as collects the fluorescence signal. The light source emits radiation in the range of 200-2000 nm. Using linear variable low-and high-pass filters, an excitation band in the visible range was selected. Two low-pass filters were used to keep leakage at higher wavelength below 0.01%. The HR2000 detector measure light signals from 400 to 850 nm and has a resolution of 0.2 nm. The shortest integration time (time to record an entire spectrum) for the detector is one millisecond. It was connected to a computer via a USB connector.

Two types of fluorescence experiments were conducted. First, experiments were conducted with a Rhodamine-6G containing membrane in a TGA to illustrate the relationship between the membrane water content and the fluorescence behavior at the fuel cell operating temperature. The 350-μm bare optical fiber was inserted into the TGA perpendicular to the membrane, which rested on a sample pan (see inset of FIG. 2). In a second series of experiments to measure the fluorescence from a functioning membrane in a fuel cell, the 350-μm bare optical fiber was embedded in the membrane. The fluorescence signal is collected form the entire thickness of the membrane and provides a thickness averaged signal.

Correlation of Fluorescence with Water Content

An initial estimate of the sensitivity of the fluorescence measurement to the membrane water content was obtained by simultaneously collecting fluorescence data during a weight loss experiment conducted in a TGA. From the Nafion® dye solution, a membrane was cast in a vial at 60° C. in an oven. A piece of the cast membrane was soaked in deionized water. The water soaked sample was placed in the TGA pan to monitor the water weight loss with simultaneous fluorescence measurement at 80° C. The furnace temperature was raised to 80° C. at 50° C./min and was held at that temperature. Excess water was added to the pan so that the membrane would not lose water before it reached 80° C. The purge gas used was dry nitrogen.

From the weight loss curve shown in FIG. 2, it is hard to distinguish the free water loss and the membrane water loss. The loss of water from the membrane is evident however, in the derivative curve. Between 0 and 12 min, the weight loss is due to the evaporation of free water. From 12 min to 22 min, water trapped below the sample and some water from the membrane evaporates. The rate of water loss decreases after 22 min, until 27 min when it approaches 0 mg/min, as observed from the derivative curve. The weight data from 22 min to 40 min was used to calculate the membrane water content. The weight of the membrane at the end of the run (i.e., at 40 min), was considered as the final dry membrane weight. We checked for complete water removal from the membrane by subjecting it to 130° C. for 5 min and we did not observed any weight loss. The membrane loses almost all of its water in the 22 min to 27 min interval.

The fluorescence behavior of Rhodamine-6G in Nafion® during the 22 to 27 min period is shown in FIG. 3. The spectra were recorded at 3-s intervals. At high water content the fluorescence showed a maximum at 553 nm and the intensity of this peak decreases with loss of water. As intensity of the peak at 553 nm decreased with loss of water, prominent shoulders at 538 and 563 nm appeared on the spectrum. The complete spectrum consists of three peaks, and their deconvolution is discussed below. The fluorescence behavior before 22 min, which is not shown, had a fluorescence maximum at 553 nm and the intensity was even higher than the intensity of the 26.6 wt % water containing spectra shown in FIG. 3.

The fluorescence behavior with water loss at room temperature followed the same trend as observed at 80° C. The intensity ratio as a function of membrane water content at 23 and 80° C. is shown in FIG. 5. The 23° C. correlation curve is included to show the effect of temperature on the fluorescence response. For determination of membrane water content in the fuel cell, the correlation at 80° C. is relevant.

A number of issues prevent the quantitative use of the 80° C. calibration curve from FIG. 5. First, the measurements at 80° C. were done under dynamic conditions in the TGA, which could distort the data due to transport limitations of water into and out of the membrane. Attempts to establish equilibrium conditions in the TGA were not successful due to high levels of noise in the weight measurement caused by a flowing gas stream of controlled humidity. Second, changes in the coupling optics between the membrane and optical fiber during the calibration experiment, due to evaporation of the free water, caused difficulty in quantitatively reproducing the 80° C. calibration curve. Nevertheless, the sigmoidal shape of the calibration curve is reproducible, indicating clearly that the fluorescence measurement provides excellent sensitivity to membrane water content.

Peak deconvolution indicates three peaks fit the observed spectra quite well at all water contents, but substantial Stokes shifts for two of the peaks are required to maintain a good fit. The fundamental fluorescence response of Rhodamine-6G in Nafion® is clearly complex, but to remain focused on the fuel cell application only a brief description of the fluorescence mechanism follows. Similar behavior of Rhodamine-6G in Nafion® membranes has been reported in the literature. In the Zhu et al. reference mentioned previously, it was proposed that Rhodamine-6G forms a complex form with water that has higher absorbance compared to an uncomplexed form, and hence the fluorescence intensity increases with water content. The Mohan and Iyer reference, also mentioned previously, reported similar behavior of rhodamine-6G in Nafion®, that is, when the wet membrane containing the dye dried in air at room temperature, the fluorescence intensity at 550 nm decreased and new peaks appeared. Mohan and Iyer suggested that Rhodamine-6G in Nafion® exists in two equilibrium forms, protonated and non-protonated.

Accordingly, the protonated form has been found to absorb at 470 nm and have generally low absorbance whereas the non-protonated form has been found to absorb at 525 nm and have relatively high absorbance. The relative fraction of the two forms depends primarily on the concentration of $H^+$ ions, (i.e. pH). At high pH, the non-protonated form dominates whereas at low pH the protonated form dominates. This was verified by monitoring the absorbance ratio A525/A470 of the membrane immersed in aqueous acidic solutions, in which it was found that the ratio decreased with increasing concentration of the $H^+$ ions.

In Nafion®, the number of sulfonic acid groups does not change unless the membrane undergoes degradation. However, with a change in water content, the dissociation of the sulfonic acid groups and hence the concentration of $H^+$ ions will change. With an increase in membrane water content the dissociation of the sulfonic acid will increase but would result in dilution of the acid groups. This will cause a pH change and the absorbance and fluorescence behavior will change. The absorbance trend of the dye-containing membrane during drying is shown in FIG. 4.

As a result of the present experimentation discussed herein, it was also found that the absorption ratio decreased with loss of water. This further indicates how the ratio of non-protonated to protonated form changes with the loss of water, that is, as the absorbance ratio decreases the protonated, less fluorescent form will dominate and the fluorescence signal would decrease. The absorbance below 480 nm increased with the loss of water. The absorbance showed large changes at 520 nm but to avoid excitation and emission overlap, an excitation band from 400-460 nm was selected for our fluorescence experiments, as the dye emits in the 500-700 nm range. Specifically, the fluorescence intensities at 552 and 620 nm were used to quantify the emission data, as they were found to vary with water content in a systematic manner.

The water absorbed by Nafion® goes into the hydrophilic ionic domains containing mostly the pendant sulfonic acid groups. The fluorescent molecule, being ionic, will remain within or at the interface of the ionic domains. With an increase in the micelle water content, the pH inside the micelle should increase, shifting the equilibrium towards the non-protonated highly fluorescent form of Rhodamine-6G.

In Situ Membrane Fluorescence

Two experiments were conducted in an operating fuel cell. In one case, the fuel humidity was changed to explore the effects on membrane water content and fuel cell performance. However, in those experiments, the fuel cell current also changed. A more quantitative experiment was conducted in which the fuel humidity was held constant and the current was controlled to precise values.

Constant Voltage with Changing Fuel Humidity

The fluorescence behavior within the membrane was monitored with the fiber optic coupled spectrometer during fuel cell operation at various humidity levels of hydrogen and oxygen fuel gases. The fluorescence spectra at different relative humidity of the feed gases, determined from their dew points, are shown in FIG. 6. The cell voltage was maintained constant at 0.2V and the cell temperature was maintained at 80° C. for all the experiments. The fluorescence signal and the current were recorded at 30 second intervals for feed gas humidity values of 100%, 75%, 50% and 35%, respectively. For proper humidification of the membrane, the cell was operated at 80° C. with 100% humidified gases for 12 h before the start of the experiment.

With a change in the humidity of the gases from 100% to 35%, the water content and the pH of the membrane are expected to decrease. The fluorescence spectrum at 100% fuel humidity shows a single peak close to 552 nm. At 75% fuel humidity the fluorescence maximum is still at 552 nm but the intensity is reduced. With further decreases in humidity, the fluorescence decreased and multiple peaks appeared, consistent with the calibration results (See FIG. 3). The changes in fluorescence behavior when humidity was changed from 100% to 50% are distinct. However the spectra at 50% and 35% are similar. This likely indicates that no significant change in the membrane water content occurred in the low fuel gas humidity range. The changes in the intensity ratio of the spectra, which permit each spectrum to be characterized by a single number, are also of note.

FIG. 7 illustrates the fluorescence intensity ratio and the current response of the cell with feed gases of different humidities. The solid line shows the intensity ratio, while the dotted line shows the current density. The fluorescence spectra illustrated in FIG. 6 were taken at the end of each period labeled in FIG. 7. FIG. 7 reveals the complex dynamic behavior of the fuel cell during startup, operational changes, and short term internal phenomena.

For example, after conditioning the cell for 12 hours, it was shut down overnight and allowed to cool. Upon startup thereafter, the cell temperature was raised from room temperature to 80° C. under a constant voltage of 0.2 V and 100% feed gas humidity. This startup period corresponds to the period from 0 to roughly 30 minutes in FIG. 7. As the cell heats up the membrane loses water due to evaporation. As the membrane loses water its proton conductivity drops, as the proton conductivity is dependant on membrane water content. This drop in water content reduces current due to drop of conductivity. The loss of water increases the concentration of sulfonic acid groups and lowers the pH inside the membrane. At low pH the protonated form of Rhodamine-6G is favored resulting in decrease in fluorescence ratio. The membrane subsequently absorbs water from the humidified gases and its conductivity increases, which increases current. This behavior may indicate water transport rate limitations at the anode/membrane interface.

At 100% humidity there were some small peaks in the current and fluorescence ratio. Although their cause is not well known, and we do not wish to be limited to one theory, we surmise they are due to minor flooding and clearing events of water from the cathode. It should be noted that these small events are not as prominent when the fuel cell is operated with 75% humidified fuel gases, and they are completely absent at the lower humidity values. At lower humidity, flooding at the cathode should not occur since the water formed will simply evaporate into the oxygen stream.

At 100% fuel gas humidity, the fluorescence ratio was near 5.8. After a 30 min shutdown near 150 min, the experiment was resumed with the humidity changed to 75%. At the beginning of the 75% humidity period, the fluorescence intensity ratio (and water content) is higher and the current density is nearly identical compared to their steady state values at 100% humidity. The increase in water content during the 30 min shutdown occurred because the cessation of the electrochemical reaction permitted back diffusion of water from the cathode into the membrane to increase the pH. Although the increased water content should have increased conductivity and current, the cathode was probably well flooded, holding down the current density when the cell was restarted. With the decrease in the humidity of the gases, the water uptake is reduced, the membrane water content falls, resulting in lower proton conductivity and current. Steady state operation at 75% gas humidity was not achieved due to incomplete data analysis in real time and therefore not waiting until the fluorescence signal reached a constant value.

An important point to note from FIG. 7 is that the membrane water content and fuel cell current do not appear to attain their steady state values at the same time. This may indicate that the local gradients within the membrane continue to change even after the macroscopic fuel cell behavior becomes steady.

Photobleaching was tested for by returning to the initial conditions of the experiment after several hours of data acquisition. The signal obtained at this end point matched the signal obtained at the beginning of the experiment very closely, and this procedure was repeated for most experiments. The signal of most interest is the fluorescence intensity ratio $I_{552}/I_{620}$, and it is this signal that did not change. Also, the Rhodamine-6G concentration in the membrane was well below the inner filtering limit. Finally, repetitive fluorescence measurements at 100% RH and 80° C. indicate that the experimental error in the fluorescence intensity ratio is less than 1%.

A reference to Hinatsu et. al. reported a water uptake value of 10 water molecules per sulfonic acid group for Nafion® 117 at 80° C. and 100% RH. This corresponds to a water content of 16.3 wt %. A reference to Rieke et. al., based on a spectroscopic technique, reported 11 water molecules per sulfonic acid group (18% water) for Nafion® 117 at 95° C. These are steady state water uptake values of Nafion® membranes equilibrated in a humidified atmosphere outside the fuel cell.

The fluorescence intensity ratio measurements in FIG. 7 at 100% RH correspond to a membrane water content of 17.8 wt % if the correlation in FIG. 5 is used. Although this value may not be very accurate due to calibration errors discussed above, it appears that the membrane water content measured in this work is in the same range as observed previously for Nafion® at 80° C. More accurate comparisons will be made in the future in order to illustrate the differences between water uptake under static conditions outside the fuel cell and the dynamic conditions inside the fuel cell. Also the membrane is coated with catalyst which could alter the water absorption kinetics.

Constant Fuel Humidity with Changing Current

FIG. 8A shows the current and voltage vs. time, and FIG. 8B shows the corresponding fluorescence intensity ratio and voltage vs. time for a series of step changes in the current. The current was increased in a stepwise manner from 0 to 1.35 A using 0.15 A steps in time intervals of 600 s. Fluorescence spectra were collected every 30 s. The cell was operated at 80° C. and fuel gases were fed at 75% relative humidity. There were some fluctuations in the cell voltage, as observed in FIG. 8A, and much larger corresponding fluctuations in the fluorescence signal, as observed in FIG. 8B. The correspondence may indicate that the voltage fluctuations are related to water content fluctuations. With an increase in current, more water is transported with the protons towards the cathode due to the increased rate of proton transfer. Nevertheless, FIG. 8B indicates that the fluorescence ratio, and hence the membrane water content, decreases as the current increases.

A decrease in the membrane water content with increase in current densities has been proposed based on an observed increase in the membrane resistance. A reference to Sridhar et. al. reported a decrease in water of solvation of protons with an increase in current density by measuring the humidity of the hydrogen inlet and outlet stream. Other known models have predicted a decrease in membrane water content with increase in current densities. The decrease in water content has been reported to be on the anode side of the membrane.

For example, a reference to Buchi and Scherer discloses experiments which shown that membrane resistance increases primarily on the anode side as current is increased. Those models and measurements suggest insufficient external humidification of the membrane and insufficient compensation of the electro-osmotic drag by the back diffusion of water.

Although not intending to be limited to any one theory, it is hypothesized that a decrease in the membrane water content with increasing current could be due to mass transfer resistance at the anode side. The resistance may be significant because of a number of phenomena such as the hydrophobic catalyst layer imprinted on the membrane surface, water absorption kinetics into the membrane and membrane processing conditions. The formation of hydronium ion can occur on the catalyst particles or at the catalyst membrane interface. In either case, non-polar hydrogen can easily reach the catalyst particles through the porous hydrophobic carbon support, but for the polar water molecule the carbon support may present a significant resistance.

The technique of the present invention can sense the membrane water content under steady and dynamic conditions, helping to understand the water transport in the membrane. For example, in additional experiments performed at 50% RH, the fluorescence intensity ratio decreased as the current was increased, just as shown in FIG. 8B for the experiments conducted at 75% RH. However, at 100% RH, the fluorescence signal did not show a significant change as the current was increased. There may not be a large change in the membrane water content with increasing current at 100% RH because the driving force for water uptake in the membrane may be large enough at 100% RH to overcome the mass transfer limitations.

The present invention provides an exemplary system and method for sensing the water content inside a membrane during fuel cell operation fluorescence using fiber optic measurements. Experimental techniques to produce the correlation curve between the fluorescence signal and the membrane water content have been disclosed, but other correlation curves can be derived to make this technique quantitative in accordance with the present invention. In principle, such measurements at different locations could probe the spatial distribution of water inside the membrane. The in-plane water distribution, for example, could be used to help design efficient gas distribution channels in accordance with the present invention.

The fluorescence behavior of rhodamine-6G in Nafion® was found to be sensitive to air humidity. Thus, humidity measurements in the gas distribution channels can be measured and related to the water activity in the membrane in accordance with the present invention. More generally, fluorescence can also be applied to many other physical and chemical measurements in accordance with the present invention. For example, by incorporating fluorescent molecules sensitive to a particular reactant, such as oxygen, its distribution in the Nafion® membrane could also be studied. Degradation products of the Nafion® membrane could also be detected with fluorescence in accordance with the present invention. Finally, fluorescence probes exist for temperature and stress measurements, and such characterizations of in situ membrane behavior as described herein according to the present invention are valuable for understanding fuel cell performance and durability.

Once again, the fluorescence measurement of membrane water content predicted the dynamic response of the fuel cell during startup, operating condition changes, and during many small perturbations. A decrease in membrane water content was observed as fuel cell current was increased. The decrease in water content is attributed to mass transfer limitations at the anode side of the membrane.

It is to be understood that the system and method of the present invention may be advantageously employed without the incorporation of each of the features disclosed herein. It is to be further understood that modifications and variations may be utilized without departure from the spirit and scope of this inventive system and method, as those skilled in the art will readily understand. Such modifications and variations are considered to be within the purview and scope of the appended claims and their equivalents.

The following list of references, which includes references that have been referred to herein above along with others that have not already been referred to, are all fully incorporated herein in their entirety.

(1) Eisenberg, A.; Yeager, H. L.; Editors *American Chemical Society Symposium Series, No.* 180: *Perfluorinated Ionomer Membranes [Developed in Advance of the Topical Workshop on Perfluorinated Ionomer Membranes*, Lake Buena Vista, Fla., Feb. 23-26, 1982], 1982.

(2) Zawodzinski, T. A., Jr.; Derouin, C.; Radzinski, S.; Sherman, R. J.; Smith, V. T.; Springer, T. E.; Gottesfeld, S. *Journal of the Electrochemical Society* 1993, 140, 1041-1047.

(3) Anantaraman, A. V.; Gardner, C. L. *Journal of Electroanalytical Chemistry* 1996, 414, 115-120.

(4) Edmondson, C. A.; Stallworth, P. E.; Chapman, M. E.; Fontanella, J. J.; Wintersgill, M. C.; Chung, S. H.; Greenbaum, S. G. *Solid State Ionics* 2000, 135, 419-423.

(5) Gebel, G. *Polymer* 2000, 41, 5829-5838.

(6) Zawodzinski, T. A.; Davey, J.; Valerio, J.; Gottesfeld, S. *Electrochimica Acta* 1995, 40, 297-302.

(7) Bunce, N. J.; Sondheimer, S. J.; Fyfe, C. A. *Macromolecules* 1986, 19, 333-339.

(8) Gonzalez-Benito, J.; Bravo, J.; Mikes, F.; Baselga, J. *Polymer* 2002, 44, 653-659.

(9) Martin, O.; Pastoriza, A.; Mikes, F.; Baselga, J. *Polymer International* 2002, 51, 1207-1210.

(10) Hakala, K.; Vatanparast, R.; Vuorimaa, E.; Lemmetyinen, H. *Journal of Applied Polymer Science* 2001, 82, 1593-1599.

(11) Miller, K. E.; Krueger, R. H.; Torkelson, J. M. *Journal of Polymer Science, Part B: Polymer Physics* 1995, 33, 2343-2349.

(12) Geuskens, G.; Soukrati, A. *European Polymer Journal* 2000, 36, 1537-1546.

(13) Otsuki, S.; Adachi, K. *Polymer Journal* (Tokyo, Japan) 1994, 26, 343-348.

(14) Bright, F. V.; Poirier, G. E.; Hieftje, G. M. *Talanta* 1988, 35, 113-118.

(15) Glenn, S. J.; Cullum, B. M.; Nair, R. B.; Nivens, D. A.; Murphy, C. J.; Angel, S. M. *Analytica Chimica Acta* 2001, 448, 1-8.

(16) Mohan, H.; Iyer, R. M. *Journal of the Chemical Society, Faraday Transactions* 1992, 88, 41-45.

(17) Mohan, H.; Iyer, R. M. *Analyst* (Cambridge, United Kingdom) 1993, 118, 929-932.

(18) Zhu, C.; Bright, F. V.; Wyatt, W. A.; Hieftje, G. M. *Proceedings—Electrochemical Society* 1987, 87-9, 476-483.

(19) Hinatsu, J. T.; Mizuhata, M.; Takenaka, H. *Journal of the Electrochemical Society* 1994, 141, 1493-1498.

(20) Rieke, P. C.; Vanderborgh, N. E. *Journal of Membrane Science* 1987, 32, 313-328.

(21) Buchi, F. N.; Scherer, G. G. *Journal of the Electrochemical Society* 2001, 148, A183-A188.

(22) Andreaus, B.; Scherer, G. G. *Solid State Ionics* 2004, 168, 311-320.

(23) Sridhar, P.; Perumal, R.; Rajalakshmi, N.; Raja, M.; Dhathathreyan, K. S. *Journal of Power Sources* 2001, 101, 72-78.

(24) Eikerling, M.; Kharkats, Y. I.; Kornyshev, A. A.; Volfkovich, Y. M. *Journal of the Electrochemical Society* 1998, 145, 2684-2699.

The invention claimed is:

1. A fuel cell system including means for unobtrusively measuring fluorescence of a membrane within a fuel cell, the membrane containing a fluorophore, the system comprising:
   a) a fuel cell including a membrane containing a fluorophore; and
   b) a sensing device for unobtrusively measuring fluorescence of the membrane, the device including a medium permitting light transfer therein having opposing ends, wherein one of the opposing ends is in contact with the membrane and wherein the other of the opposing ends is operatively associated with a light source and a spectrometer.

2. The system as recited in claim 1, wherein the medium is an optical fiber.

3. The system as recited in claim 1, wherein the end of the medium operatively associated with the light source and the spectrometer is bifurcated.

4. The system as recited in claim 1, wherein the membrane is a polymer electrolyte membrane (PEM).

5. The system as recited in claim 1, wherein the membrane includes a perfluorinated sulfonic acid ionomer.

6. The system as recited in claim 1, wherein the fluorophore is sensitive to membrane water content, and wherein membrane water content is determined based on the fluorescence measurement.

7. The system as recited claim 6, wherein the fluorophore is rhodamine-6G.

8. The system as recited in claim 1, wherein the membrane is ionomeric.

9. The system as recited in claim 1, wherein the fluorophore exists in either a protonated or non-protonated form, wherein the protonated form and non-protonated form absorb light at different wavelengths.

10. The system as recited in claim 1, wherein the fluorophore is sensitive to a reactant in the membrane and wherein the measuring fluorescence is used to determine the distribution of the reactant in the membrane.

11. The system as recited in claim 1, wherein the fluorophore is sensitive to temperature or stress in the membrane and wherein the measuring fluorescence is used to determine fuel cell performance or durability.

12. The system as recited in claim 1, wherein the end in contact with the membrane is embedded in the membrane.

13. A method for unobtrusively measuring fluorescence of a membrane within a fuel cell, the membrane containing a fluorophore, the method comprising steps of:
   a) inserting a medium permitting light transfer therein having opposing ends, wherein one of the opposing ends is in contact with a membrane within a fuel cell, the membrane containing a fluorophore therein, and wherein the other end is operatively associated with a light source and a spectrometer;
   b) activating the light source; and
   c) measuring fluorescence of the membrane using the spectrometer.

14. The method according to claim 13, further comprising a step of measuring a dynamic response of the fuel cell during at least one of: (i) startup, (ii) operating condition changes, and (iii) a plurality of small perturbations.

15. The method according to claim 13, wherein the fluorophore is sensitive to membrane water content, the method further comprising a step of correlating the fluorescence of the membrane to membrane water content.

16. The method according to claim 15, wherein the fluorophore exists in either a pronated or non-pronated form, the pronated form and non-pronated form absorbing light at different wavelengths, wherein the measuring the fluorescence of the membrane includes measuring the fluorescence at the two different wavelengths, and wherein the correlating the fluorescence of the membrane to membrane water content includes steps of:
   a) calculating an absorbance ratio as between the two different wavelengths,
   b) determining an ion concentration based on the calculated ratio, and
   c) determining membrane water content based on the ion concentration.

17. A sensing device for unobtrusively measuring fluorescence of a membrane within a fuel cell, the membrane containing a fluorophore, the device comprising a medium permitting light transfer therein having opposing ends, wherein one of the opposing ends is adapted to contact a membrane within a fuel cell, the membrane containing a fluorophore, and wherein the other of the opposing ends is operatively associated with a light source and a spectrometer.

18. The device as recited in claim 17, wherein the medium is an optical fiber.

19. The device as recited in claim 17, wherein the end of the medium operatively associated with the light source and the spectrometer is bifurcated.

20. The device as recited in claim 17, wherein the end adapted to contact the membrane is coated with the same material forming the membrane.

* * * * *